United States Patent
Hsieh et al.

(10) Patent No.: US 12,298,243 B2
(45) Date of Patent: May 13, 2025

(54) SYSTEMS AND METHODS FOR AUTOMATED ROTATIONAL ACTUATOR FOR TESTING OF A PHOTOPLETHYSMOGRAM SENSOR

(71) Applicant: PLUME DESIGN, INC., Palo Alto, CA (US)

(72) Inventors: Min-Feng Hsieh, Tainan (TW); Ta-Lung Lee, New Taipei (TW); Shu-Hua Chang, Zhubei (TW); Zhicheng Qiu, Cupertino, CA (US)

(73) Assignee: PLUME DESIGN, INC., Palo Alto, CA (US)

(*) Notice: Subject to any disclaimer, the term of this patent is extended or adjusted under 35 U.S.C. 154(b) by 183 days.

(21) Appl. No.: 18/318,037

(22) Filed: May 16, 2023

(65) Prior Publication Data

US 2024/0385112 A1    Nov. 21, 2024

(51) Int. Cl.
*G01N 21/55*    (2014.01)
*A61B 5/024*    (2006.01)

(52) U.S. Cl.
CPC .......... *G01N 21/55* (2013.01); *A61B 5/02416* (2013.01); *G01N 2201/127* (2013.01)

(58) Field of Classification Search
CPC .............. G01N 21/55; G01N 2201/127; A61B 5/02416
See application file for complete search history.

(56) References Cited

U.S. PATENT DOCUMENTS

2016/0206221 A1*   7/2016   Kim ...................... A61B 5/681

FOREIGN PATENT DOCUMENTS

| | | | | |
|---|---|---|---|---|
| CN | 115462782 A | * | 12/2022 | ........... A61B 5/0205 |
| FR | 3088117 A1 | * | 5/2020 | ......... A61B 5/02055 |

* cited by examiner

*Primary Examiner* — Jonathan M Hansen
*Assistant Examiner* — Jarreas Underwood
(74) *Attorney, Agent, or Firm* — Nicholas Martin; Greenberg Traurig, LLP

(57) ABSTRACT

Systems and methods of embodiments of the present disclosure provide automated testing of PPG sensors using a programmatically controlled rotational actuator. The rotational actuator may include one or more light reflecting surfaces that can be actuated towards and away from the PPG sensor to simulate reflectivity of the tissue of a subject. Particular heart rates, heart rate variabilities and/or other physiological behaviors may be simulated based on actuations patterns, including, e.g., frequency, range of actuation, or variations thereof, among other actuation pattern characteristics. Based on the output signal produced by the PPG sensor in response to the actuation pattern, the PPG sensor may be assessed for accuracy and/or sensitivity to ensure quality.

20 Claims, 4 Drawing Sheets

SYSTEMS AND METHODS FOR AUTOMATED ROTATIONAL ACTUATOR FOR TESTING OF A PHOTOPLETHYSMOGRAM SENSOR

FIELD OF TECHNOLOGY

The present disclosure generally relates to an automated rotational actuator and systems and methods of control thereof for automated testing of a photoplethysmogram (PPG) sensor.

BACKGROUND OF TECHNOLOGY

A PPG is an optically obtained plethysmogram that can be used to detect blood volume changes in the microvascular bed of tissue. A PPG sensor may detect a time varying light absorbance signal ("PPG" signal) in order to detect time-varying blood volume changes to, e.g., measure heart rate and/or heart rate variability. The time varying PPG signal may be affected by a number of factors, some of which include the optical properties of the tissues and blood at the measurement site, volume of arteries near the skin's surface and the wavelength of the light source.

SUMMARY OF DESCRIBED SUBJECT MATTER

In some embodiments, PPG sensors may measure the time varying PPG sensor based on reflected light. Thus, a PPG sensor may emit light onto the skin of a subject. While much of the light may be absorbed by the skin and tissue of the subject, at least a portion may be reflected back to the PPG sensor. A photo-detector (PD) may detect the reflected light, and as light varies through time, the blood volume changes in the tissue may be determined to determine physiological measurements such as heart rate and heart rate variability, among others.

Because the PPG sensor relies on reflected light from the tissue of the subject, the PD may be designed to operate at a sensitivity level sufficient to detect variations in the reflected light. But not all PDs may be of sufficient quality for such detection. Thus, each PD and/or a sample of PDs may be tested to ensure quality. But testing each PD on a human may be impractical to testing large numbers of PDs due to time and personnel/test subject constraints, as well as an inability to control with precision the physiological measurement of each human to ensure accuracy of each PD.

Thus, embodiments of the present disclosure provide automated testing of PPG sensors using a programmatically controlled rotational actuator. The rotational actuator may include one or more light reflecting surfaces that can be actuated towards and away from the PPG sensor to simulate reflectivity of the tissue of a subject. Particular heart rates, heart rate variabilities and/or other physiological behaviors may be simulated based on actuations patterns, including, e.g., frequency, range of actuation, or variations thereof, among other actuation pattern characteristics. Based on the physiological measurement output by the PD in response to the actuation pattern, the PPG sensor may be assessed for accuracy and/or sensitivity to ensure quality.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

DETAILED DESCRIPTION

Figure 1:
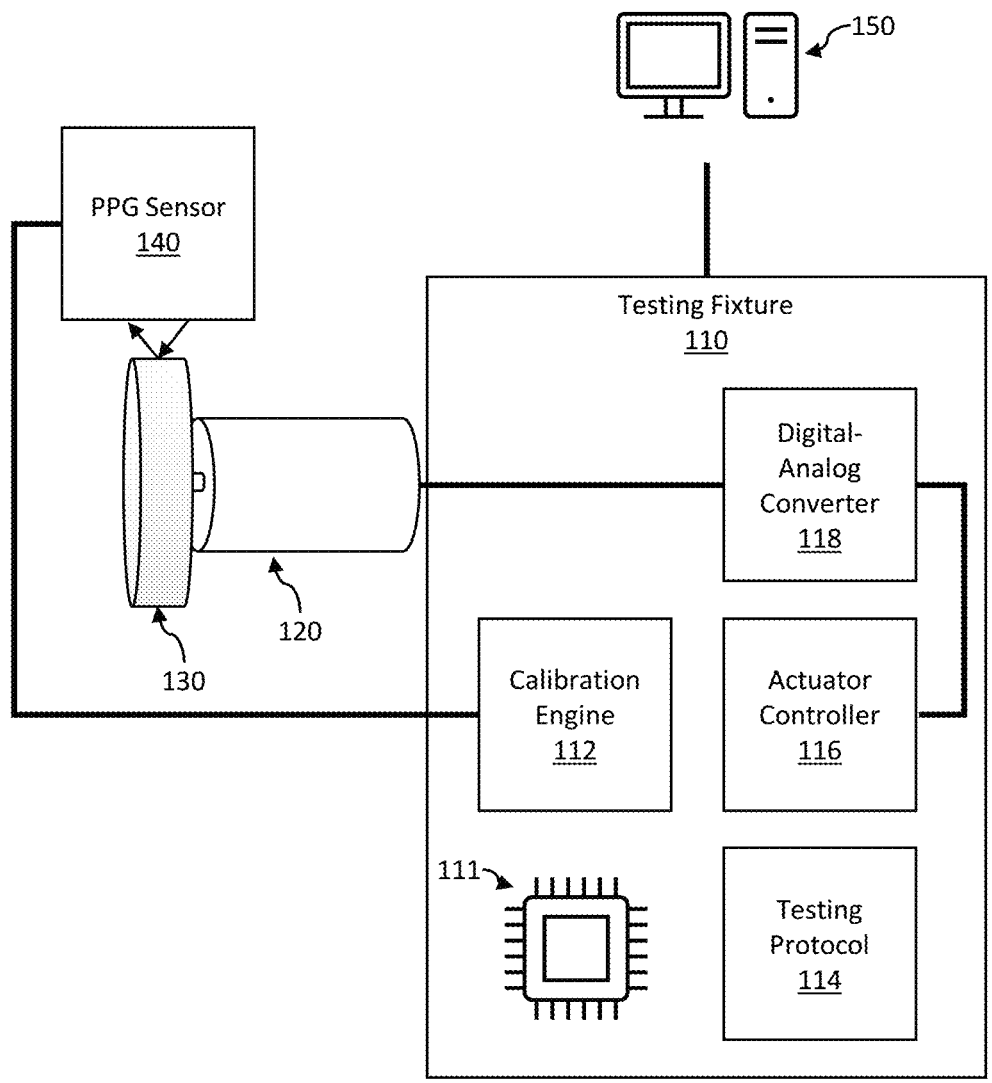
FIG. 1 depicts a testing fixture for automated testing and calibration of PPG sensor devices in accordance with one or more embodiments of the present disclosure.

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the terms "and" and "or" may be used interchangeably to refer to a set of items in both the conjunctive and disjunctive in order to encompass the full description of combinations and alternatives of the items. By way of example, a set of items may be listed with the disjunctive "or", or with the conjunction "and." In either case, the set is to be interpreted as meaning each of the items singularly as alternatives, as well as any combination of the listed items.

FIGS. 1 through 4 illustrate systems and methods of automated PPG sensor testing for calibration and/or validation of devices employing a PPG sensor, such as wearable devices (e.g., smartwatches, smart rings, smart bands, etc.), medical PPG devices, among others or any combination thereof. The following embodiments provide technical solutions and technical improvements that overcome technical problems, drawbacks and/or deficiencies in the technical fields involving PPG measurement and analysis (e.g., physiological measurement monitoring for medical and/or consumer devices). Such technical problems may involve variability and/or inconsistency of PGG sensor sensitivity and accuracy when incorporated into devices. Such PPG sensors may have some degree of inconsistency from one sensor to another due to manufacturing tolerances and other factors.

As explained in more detail, below, technical solutions and technical improvements herein include aspects of improved testing equipment that enable automated, controlled and consistent testing of PPG sensors and/or devices incorporating PPG sensors. To ensure that a device may operate effectively, e.g., with a threshold degree of accuracy between an output signal and an actual condition of a subject, the PPG sensor may be tested using simulated physiology. The simulated physiology, e.g., via a reflective cylinder or disc driven by a rotational actuator, enables a testing fixture to controllably define the physiological behavior to be measured and assess the accuracy of the PPG sensor in measuring the physiological behavior. Based on the accuracy, the PPG sensor may be calibrated for improved accuracy and/or discarded as defective. Such technical solutions enable efficient, scalable testing and/or calibration for improved device accuracy.

Based on such technical features, further technical benefits become available to users and operators of these systems and methods. Moreover, various practical applications of the disclosed technology are also described, which provide further practical benefits to users and operators that are also new and useful improvements in the art.

Referring now to FIG. 1, a testing fixture for automated testing and calibration of PPG sensor devices is illustrated in accordance with one or more embodiments of the present disclosure.

In some embodiments, a testing fixture 110 may drive a rotational actuator 120 to rotate a variable reflectivity disc 130 according to a testing protocol 114. In some embodiments, the testing fixture 110 may include one or more software and/or hardware components for performing automated testing of a PPG sensor 140 based on a sensor testing parameters selected and/or input by a user via a user computing device 150. The sensor testing parameters may be defined according to a particular simulated physiological behavior for which the PPG sensor 140 is to be tested.

Accordingly, in some embodiments, the testing fixture 110 may use the sensor testing parameters to identify and/or generate a testing protocol 114 defining an actuation pattern. Based on the actuation pattern, in some embodiments, the testing fixture 110 may implement an actuator controller 116 to generate control signals configured to cause the rotational actuator 120 to actuate according to the actuation pattern. The testing fixture 110 may also include a digital-to-analog (DA) converter 118 to provide analog control signals to control the rotational actuator 120. In some embodiments, the PPG sensor 140 may continuously or periodically measure reflectivity and/or reflectivity variations as the variable reflectivity disc 130 to output time-varying PPG sensor data. In some embodiments, the testing fixture 110 may employ a calibration engine 112 to receive time-varying PPG sensor data from the PPG sensor 140 in response to the actuation of the variable reflectivity disc 130 to determine an error and/or to calibrate the PPG sensor 140.

In some embodiments, the testing fixture 110 may include hardware components such as a processor 111, which may include local or remote processing components. In some embodiments, the processor 111 may include any type of data processing capacity, such as a hardware logic circuit, for example an application specific integrated circuit (ASIC) and a programmable logic, or such as a computing device, for example, a microcomputer or microcontroller that include a programmable microprocessor. In some embodiments, the processor 111 may include data-processing capacity provided by the microprocessor. In some embodiments, the microprocessor may include memory, processing, interface resources, controllers, and counters. In some embodiments, the microprocessor may also include one or more programs stored in memory.

Similarly, the testing fixture 110 may include storage, such as one or more local and/or remote data storage solutions such as, e.g., local hard-drive, solid-state drive, flash drive, database or other local data storage solutions or any combination thereof, and/or remote data storage solutions such as a server, mainframe, database or cloud services, distributed database or other suitable data storage solutions or any combination thereof. In some embodiments, the storage may include, e.g., a suitable non-transient computer readable medium such as, e.g., random access memory (RAM), read only memory (ROM), one or more buffers and/or caches, among other memory devices or any combination thereof.

In some embodiments, the testing fixture 110 may employ computer engines to implement the calibration engine 112, the actuator controller 116, DA converter 118 and/or the testing protocol 114. In some embodiments, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some embodiments, the calibration engine 112, the actuator controller 116, DA converter 118 and/or the testing protocol 114 may include dedicated and/or shared software components, hardware components, or a combination thereof. For example, the calibration engine 112, the actuator controller 116, DA converter 118 and/or the testing protocol 114 may each include a dedicated processor and storage. However, in some embodiments, one or more of the calibration engine 112, the actuator controller 116, DA converter 118 and/or the testing protocol 114 may share hardware resources, including the processor 111 and storage of the testing fixture 110 via, e.g., a bus.

In some embodiments, the variable reflectivity disc 130 may include a cylindrical and/or disc shaped component having a thickness in an axial direction. In some embodiments, the variable reflectivity disc 130 may include an exterior having a first end proximal to a drive shaft of the rotational actuator 120, and a second end distal to the drive shaft. In some embodiments, the exterior may further include an outer wall that extends in an axial direction between the first end and the second end of the variable reflectivity disc 130. In some embodiments, the variable reflectivity disc 130 may be hollow within an area defined by the first end, the second end and the outer wall, or may be a single solid disc. In some embodiments, the variable reflectivity disc 130 may have an internal structure within the area defined by the first end, the second end and the outer wall, where the internal structure provides support to maintain the shape and integrity of the exterior.

In some embodiments, the outer wall of the variable reflectivity disc 130 may include a surface treatment that varies across the outer wall to create variations in the reflectivity of the outer wall of the variable reflectivity disc 130. For example, in some embodiments, the rotational actuator 120 rotates the variable reflectivity disc 130 such that a surface of the outer wall moves with respect to the PPG sensor 140. As a result, as the variable reflectivity disc 130 rotates, the PPG sensor 140 senses a patch which shifts along the surface of the outer wall corresponding with the rotation. Accordingly, the variation in reflectivity may vary around the circumference of the variable reflectivity disc 130 such that as the patch to which the PPG sensor 130 is directed shift, the reflectivity varies according to the pattern of reflectivity.

In some embodiments, the pattern of reflectivity may include a gradient of reflectivity, one or more bands of reflectivity (e.g., stripes, a scale of reflectivity, alternating reflectivity, etc.), or other pattern or any combination thereof. In some embodiments, the pattern of reflectivity may be designed according to a degree to which the sensitivity of the PPG sensor 140 to variations in reflectivity is being tested. For example, the testing may be configured to test whether the PPG sensor 140 can accurately detect a continuum or intervals of reflectivity in a subject, and thus the variable reflectivity disc 130 may have a corresponding degree of variation in reflectivity (e.g., a continuum or gradient, or a corresponding number of intervals of reflectivity, respectively). In some embodiments, the testing may be effective with two levels of reflectivity, e.g., reflective and non-reflective such that the ability of the PPG sensor 140 to accurately detect the reflective and/or non-reflective portions of the variable reflectivity disc 130 during rotation is enough to satisfy the testing.

In some embodiments, reflectivity may be affected by a texture of a surface. For example, a polished surface may be more reflective than a satin or matte texturing. Thus, in some embodiments, the surface treatment may include, e.g., a texturing that ranges from a smooth polished texture to a matte or frosted texturing according to the pattern of reflectivity. In some embodiments, the texturing may be formed by an abrasive process such as contact abrasion with an abrasive pad, stone, or other object (e.g., wire brush, sand paper, emery cloth, etc.), or projectile abrasion such as sand blasting, among other abrasion techniques or any combination thereof. In some embodiments, a masking may be applied where the mask preserves the texture of masked portions, and then the abrasive process roughens the exposed portions. As a result, the pattern of reflectivity may be applied to the surface of the outer wall of the variable reflectivity disk 130.

In some embodiments, reflectivity may be affected by a coating, such as a paint, a lacquer, a plating, a galvanization, adhesive (e.g., tape, glued on coating, etc.) among other coatings or any combination thereof. The coating may be applied via a coating process such as, e.g., spray painting, electroplating, galvanization, adhesive application, among other processes or any combination thereof. In some embodiments, a masking may be applied where the mask preserves the surface treatment (e.g., any coatings or lack thereof) of masked portions, and then the coating process applies a coating to the exposed portions. As a result, the pattern of reflectivity may be applied to the surface of the outer wall of the variable reflectivity disk 130.

In some embodiments, the variable reflectivity disk 130 may be attached to the drive shaft of the rotational actuator 120. In some embodiments, the variable reflectivity disk 130 may be attached, e.g., via insertion of the drive shaft into a hub of the variable reflectivity disk 130, e.g., with a keyed, splined or friction fitment to fix the variable reflectivity disk 130 to the drive shaft. In some embodiments, the variable reflectivity disk 130 may be bolted and/or adhered to a flank on the drive shaft. In some embodiments, the variable reflectivity disk 130 may be integrally formed on the drive shaft.

In some embodiments, the rotational actuator 120 may actuate to cause the drive shaft to rotate, thus rotating the variable reflectivity disk 130. In some embodiments, the rotational actuator 120 may be any suitable device for converting an electrical signal into continuous rotation and/or rotation through one or more fixed angular positions. For example, the rotational actuator 120 may include, e.g., a stepper motor, a server motor, a fluid power actuator (e.g., that actuates a linear piston to produce rotation of the drive shaft through gearing) such as a hydraulic, pneumatic and/or vacuum actuator, among other actuators or any combination thereof.

In some embodiments, the rotational actuator 120 may include a position encoder. In some embodiments, the position encoder may include one or more devices for detecting the angular motion of the drive shaft to determine an angular position thereof, e.g., as an absolute position (an "absolute encoder") or as changes to angular position (an "incremental encoder"). In some embodiments, the position encoder may include one or more mechanical, optical, magnetic and/or capacitive encoders. Thus, the position encoder may be indexed to the reflectivity pattern such that a position detected by the position encoder may be correlated to a reflectivity on the surface of the outer wall of the variable reflectivity disk 130.

In some embodiments, the rotational actuator 120 may be controlled to rotate the variable reflectivity disk 130 to present a particular portion of the surface of the outer wall as the patch to be sensed by the PPG sensor 140. As a result, the rotational actuator 120 may be controlled to present a particular reflectivity to the PPG sensor 140. In some embodiments, the rotational actuator 120 may successively present a series of portions of the surface of the outer wall to the PPG sensor 140 based on a testing protocol. The testing protocol may define an expected output signal from the PPG sensor 140 so as to evaluate the accuracy of the PPG sensor 140 in producing an output signal that matches the expected output signal.

In some embodiments, the testing protocol 114 may include an actuation pattern that is design to match the expected output signal. For example, the testing protocol 114 may be a "normal heart rate" testing protocol that includes testing parameters corresponding to the blood flow and/or heart rate of a 60 beats per minute heart rate. Thus, the actuator pattern may establish a series of reflectance levels that would be expected to be measured as the 60 beats per minute heart rate, e.g., by presenting one or more particular levels of reflectance 60 times per minute for a particular amount time period each time in order to simulate the one or more stages in the cardiac cycle. For example, a relative higher level of reflectance may be associated with a ventricular ejection stage of the cardiac cycle, whereas a relative lower level of reflectance may be associated with a ventricular filling stage based on the effects of each stage on blood flow, with or without one or more additional intermediate levels of reflectance.

Accordingly, in some embodiments, a user may define a testing protocol to test the accuracy of the PPG sensor 140 in producing an output signal that matches a particular expected output signal. The user may interface with a graphical user interface (GUI) of the user computing device 150 to select one or more sensor testing parameters, such as, e.g., a cardiac-related condition to simulate and test (e.g., a heart rate, heart rate variability, heart rate pattern such as a heart rate pattern indicative of, e.g., angina, atrial fibrillation, ventricular fibrillation, among others), or an artificial heart rate pattern, such as a sequence of multiple levels of reflectance for a specified period of time each not corresponding to a natural heart rate pattern. In some embodiments, the sensor testing parameters may define a custom testing protocol 114 with user specified cardiac behaviors, such as, e.g., heart rate, heart rate variability, and other characteristics of cardiac behavior. In some embodiments, the sensor testing parameters may include, e.g., a number of reflectance levels, a frequency of switching between reflectance levels, a duration of presentation of each reflectance level, a number of times to switch between reflectance levels, an amount of time for the testing protocol, among other sensor testing parameters or any combination thereof.

In some embodiments, the testing fixture 110 may receive, from the computing device 150, the sensor testing parameters defined by the user. Therefore, in some embodiments, the testing fixture 110 be in communication with the user computing device 150 via one or more computer interfaces. In some embodiments, one or more computing interfaces may utilize one or more software computing interface technologies, such as, e.g., Common Object Request Broker Architecture (CORBA), an application programming interface (API) and/or application binary interface (ABI), among others or any combination thereof. In some embodiments, an API and/or ABI defines the kinds of calls or requests that can be made, how to make the calls, the data formats that should be used, the conventions to follow, among other requirements and constraints. An "application programming interface" or "API" can be entirely custom, specific to a component, or designed based on an industry-standard to ensure interoperability to enable modular programming through information hiding, allowing users to use the interface independently of the implementation. In some embodiments, CORBA may normalize the method-call semantics between application objects residing either in the same address-space (application) or in remote address-spaces (same host, or remote host on a network).

In some embodiments, one or more computing interfaces may utilize one or more hardware computing interface technologies, such as, e.g., Universal Serial Bus (USB), IEEE 1394 (FireWire), Ethernet, Thunderbolt™, Serial ATA (SATA) (including eSATA, SATAe, SATAp, etc.), among others or any suitable combination thereof.

In some embodiments, the testing fixture 110 be in communication with the user computing device 150 via one or more network connections. In some embodiments, the network may include any suitable computer network, including, two or more computers that are connected with one another for the purpose of communicating data electronically. In some embodiments, the network may include a suitable network type, such as, e.g., a public switched telephone network (PTSN), an integrated services digital network (ISDN), a private branch exchange (PBX), a wireless and/or cellular telephone network, a computer network including a local-area network (LAN), a wide-area network (WAN) or other suitable computer network, or any other suitable network or any combination thereof. In some embodiments, a LAN may connect computers and peripheral devices in a physical area by means of links (wires, Ethernet cables, fiber optics, wireless such as Wi-Fi, etc.) that transmit data. In some embodiments, a LAN may include two or more personal computers, printers, and high-capacity disk-storage devices, file servers, or other devices or any combination thereof. LAN operating system software, which interprets input and instructs networked devices, may enable communication between devices to: share the printers and storage equipment, simultaneously access centrally located processors, data, or programs (instruction sets), and other functionalities. Devices on a LAN may also access other LANs or connect to one or more WANs. In some embodiments, a WAN may connect computers and smaller networks to larger networks over greater geographic areas. A WAN may link the computers by means of cables, optical fibers, or satellites, cellular data networks, or other wide-area connection means. In some embodiments, an example of a WAN may include the Internet.

In some embodiments, the user computing device 150 may include or be incorporated, partially or entirely into at least one personal computer (PC), laptop computer, ultra-laptop computer, tablet, touch pad, portable computer, hand-held computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

In some embodiments, the testing fixture 110 may determine a testing protocol associated with the sensor testing parameters. For example, the sensor testing parameters may be associated with a particular testing protocol 114 stored in the storage of the testing fixture 110, such as, e.g., where the user specifies a particular cardiac condition. In some embodiments, the sensor testing parameters may define a custom testing protocol 114 with user specified cardiac behaviors, such as, e.g., heart rate, heart rate variability, and other characteristics of cardiac behavior. In some embodiments, store the testing protocol 114 in the storage. In such a case, the testing fixture 110 may generate the testing protocol 114 based on the custom sensor testing parameters.

In some embodiments, the actuator controller 116 may access the testing protocol 114 to generate a control signal configured to cause the rotational actuator 120 to rotate the variable reflectance disk 130 to present a series of reflectance levels to the PPG sensor 140 based on the sensor testing parameters. To do so, in some embodiments, the actuator controller 116 may extract the cardiac behavior characteristics from the testing protocol, including, e.g., frequencies and/or durations of each stage in the cardiac cycle. For example, the testing protocol 114 may include the expected output signal, including peaks and troughs in a time-varying signal. The actuator controller 116 may correlate the peaks of the time-varying signal to high reflectance periods, and the troughs to low reflectance periods, and/or anything in between a peak and a trough.

In some embodiments, the time-varying signal may be sampled with a particular resolution, such as a particular, e.g., bit depth. The resolution may define a number of discrete values that can be represented over the range of the magnitudes of the time-varying signal. Thus, the actuator controller 116 may sample a period within the time-varying signal of the testing protocol 114 and determine a magnitude, e.g., based on a mean and/or median magnitude within the sample period. The magnitude may be rounded to a nearest value of the set of discrete values to create a single value for that sample period. In some embodiments, the resolution, and thus the set of discrete values, may be configured to be equal to or less than the number of levels of reflectance provided on the variable reflectance disc 130 to ensure that all levels in the set of discrete values can be represented with a corresponding level of reflectance.

In some embodiments, the testing protocol 114 may use a sampled representation rather than a time-varying signal to represent the sensor testing parameters. As a result, the actuator controller 116 may omit the step for sampling the testing protocol 114. For example, the testing protocol 114 may include a bit depth of two such that the testing protocol 114 may be represented as a sequence of binary levels, high and low.

In some embodiments, the actuator controller 116 may have an index of reflectance levels to rotational actuator 120 positions. Thus, the actuator controller 116 may translate the levels in the set of discrete values that represent the testing protocol 114 to the corresponding level of reflectance. Thus, the sampled representation may be converted or translated to a sequence of levels of reflectance. In some embodiments, the actuator controller 116 may then map the levels of reflectance in the sequence to positions of the rotational actuator 120 to define an actuator pattern.

In some embodiments, the testing of the PPG sensor 140 may be configured to test the ability of the PPG sensor 140 to detect the highest and lowest level of reflectance expected in a subject. Thus, in some embodiments, to improve efficiency, the testing protocol 114 may be a sequence of peaks and troughs according to a particular frequency and/or duration of each peak and/or trough.

In some embodiments, the testing protocol 114 may be the actuator pattern and/or the sequence of levels of reflectance rather than an expected output signal. Thus, the testing protocol 114 may be selected from a library or configured based on the user selections at the user computing device 150. As a result, the actuator controller 116 may omit the sampling, translation and mapping steps.

In some embodiments, the actuator controller 116 may output the actuator pattern as a digital signal. In some embodiments, to convert the digital signal to a control signal that operates the rotational actuator 120, the DA converter 118 may convert the digital signal to an analog signal. In some embodiments, the DA converter 118 may convert an abstract finite-precision number (such as a fixed-point binary number) into a physical quantity (e.g., a voltage or a pressure) to convert finite-precision time series data of the digital signal of the actuation pattern to a continually varying physical signal.

In some embodiments, the DA converter 118 may include, e.g., a pulse-width modulator (PWM), an oversampling DA converter, an interpolating DA converter, a binary-weighted DA converter, a cyclic DA converter, a thermometer-coded DA converter, a hybrid DA converter, among other DA converters or any combination thereof.

In some embodiments, the digital signal may not provide enough power to drive the rotational actuator 118. Thus, in addition to converting the digital signal to an analog signal, the DA converter 118 may include an amplifier. In some embodiments, amplifier may be a separate piece of equipment or an electrical circuit within the DA converter 118. Indeed, the amplifier may be a separate piece of equipment from the testing fixture 110 or an electrical circuit within the testing fixture 110. In some embodiments, the amplifier may increase the power of the analog signal to a level sufficient to drive the rotational actuator 120.

In some embodiments, the DA converter 118 may provide the analog signal of the actuator pattern to the rotational actuator 120. In some embodiments, the DA converter 118 and/or the actuator controller 116 may receive from the rotational actuator 120, real-time position data indicative of the of the position of the variable reflectivity disc 130 based on the position encoder. In some embodiments, the DA converter 118 and/or the actuator controller 116 may include an index that maps positions to levels of reflectivity. Thus, based on the position reported by the position encoder, the DA converter 118 and/or the actuator controller 116 may emit control signals for each level of reflectance in the actuation pattern so as to cause the rotational actuator 120 to rotate the variable reflectivity disc 130 to a position of a next level of reflectivity in the sequence.

In some embodiments, the DA converter 118 and/or the actuator controller 116 may be configured to control the rotational actuator 120 to rotate the drive shaft in one or both directions. For example, the DA converter 118 and/or the actuator controller 116 may control the rotational actuator 120 to simulate a continuous signal by rotating in one direction through a gradient of levels of reflectivity on the variable reflectivity disc 130. To do so, the DA converter 118 and/or the actuator controller 116 may modulate the speed of rotation such that each level of reflectivity in the actuator pattern is positioned in the patch sensed by the PPG sensor 140 for the correct duration, and the levels of reflectivity are switch according to the correct frequency, with the levels of reflectivity in between positionings providing a continuous transition between levels of reflectivity. Such a control scheme may also be applied to a variable reflectivity disc 130 having discrete steps in reflectivity throughout the circumference. Whether discrete steps or a continuous gradient, the levels of reflectivity of the variable reflectivity disc 130 may be oscillatory, such that throughout a full turn of the variable reflectivity disc 130 progresses from peak to trough and back to peak.

In some embodiments, the DA converter 118 and/or the actuator controller 116 may use the real-time position data to determine a current angular position, determine a next angular position associated with a next level of reflectance in the actuator pattern, and skip the rotation to the next angular position. Thus, the DA converter 118 and/or the actuator controller 116 may control the rotational actuator 130 to rotate the drive shaft in either direction to rotate to the next angular position with a least amount of rotation. However, the DA converter 118 and/or the actuator controller 116 may control the rotational actuator 130 to rotate the drive shaft in one direction and thus may always rotate in the one direction to achieve the next angular position.

In some embodiments, the actuator pattern may include two levels of reflectivity. Thus, the DA converter 118 and/or the actuator controller 116 may control the rotational actuator 120 to rotate back and forth between the two levels of reflectivity on the variable reflectivity disc 130.

As a result, in some embodiments, the DA converter 118 and/or the actuator controller 116 may control the rotational actuator 120 to rotate the variable reflectivity disc 130 to achieve a sequence of angular positions to present to the PPG sensor 140 a sequence of levels of reflectivity that simulate the variation in reflectivity in a subject exhibiting the cardiac behavior. Accordingly, the PPG sensor 140 may output time-varying PPG sensor data that measures the time-varying reflectivity that simulates the cardiac behavior. As result, in some embodiments, the performance of the PPG sensor 140 may be assessed based on the degree to which the time-varying PPG sensor data matches the expected output signal.

In some embodiments, to do so, the calibration engine 112 of the testing fixture 110 may receive the time-varying PPG sensor data and compare the time-varying PPG sensor data to the expected output signal and/or the actuator pattern. In some embodiments, to enable the comparison between the output signal and the expected output signal/actuator pattern, the output signal may be synchronized with the expected output signal/actuator pattern to align the data in time. Thus, the reflectivity measured by the PPG sensor 140 at any given time may be compared to the reflectivity defined by the actuation pattern at the same given time.

In some embodiments, the calibration engine 112 may calculate an error based on a deviation between the time-varying PPG sensor data and the expected output signal and/or the actuator pattern. For example, the calibration engine 112 may measure a deviation through time between the time-varying PPG sensor data and the expected output signal and/or the actuator pattern. Based on the deviation through time, the calibration engine 112 may generate an error metric indicative of the deviation through time, such as, e.g., by calculating an average, median, or other statistical metric of the deviation through time.

In some embodiments, the calibration engine 112 may calculate the error as a number or frequency of mismatches between the output signal and the expected output signal/ actuation pattern. A mismatch may include one level of reflectivity measured by the PPG sensor 140 and a different level of reflectivity define in the actuation pattern for the same time.

In some embodiments, where the error, including the deviation and/or the number of mismatches, exceeds a predetermined threshold, the calibration engine 112 may determine that the PPG sensor 140 is defective. In some embodiments, the predetermined threshold may be a measure relative to a baseline. For example, for a deviation in amplitude, the predetermined threshold may signify a maximum allowable percent deviation from a baseline amplitude, such as, e.g., e.g., 15, 16, 17, 18, 19, 20, 21, 22, 23, 24, 25 or more percent relative to a relative signal amplitude change, or any other percent deviation in a range of about, e.g., 10 to 40 percent. In another example, for a deviation in the time domain, the predetermined threshold may signify a maximum allowable percent deviation from a baseline deviation in time, such as, e.g., e.g., 1, 2, 3, 4, 5, 6, 7, 8, 9, 10 or more percent relative to a relative time-based change (e.g., based on sensor sampling rate such as 50 Hertz (Hz)), or any other percent deviation in a range of about, e.g., 0.1 to 20.0 percent. In another example, for a deviation in the frequency domain, the predetermined threshold may signify a maximum allowable percent deviation from a baseline deviation in frequency, such as, e.g., e.g., 1, 2, 3, 4, 5, 6, 7, 8, 9, 10 or more percent relative to a relative frequency-based change (e.g., based on a signal range such as between 0.015 and 0.4 Hz), or any other percent deviation in a range of about, e.g., 0.1 to 20.0 percent. In some embodiments, the predetermined threshold may be different for the deviation than the number of mismatches, or may be for a combination of the deviation and the number of mismatches (e.g., a weighted sum, a sum, or other function or any combination thereof). Where the PPG sensor 140 is defective, the testing fixture 110 may output to the user computing device, e.g., via the graphical user interface, an alert indicating that the PPG signal under test is defective.

In some embodiments, where the deviation does not exceed a predetermined threshold, the calibration engine 112 may determine offset or bias of the PPG sensor 140 that indicates a degree to which the PPG sensor 140 produces an output signal is above or below the expected output signal and/or actuation pattern according to the deviation. In some embodiments, the calibration engine 112 may reprogram the PPG sensor 140 to apply the offset to the measurements of the PPG sensor 140. As a result, the offset may compensate for the deviation in the measurements of the PPG sensor 140 to improve the accuracy of the PPG sensor 140.

Figure 2:
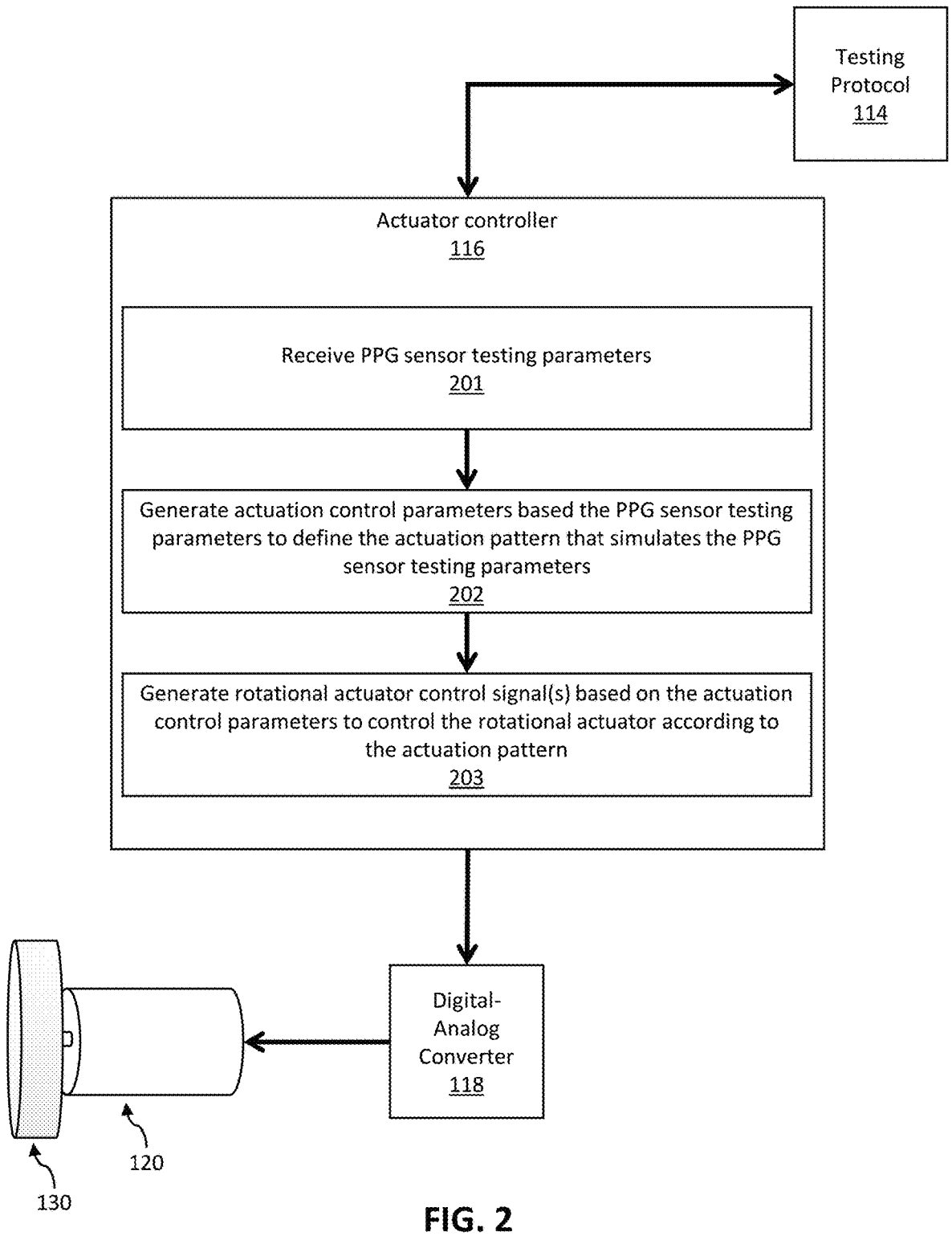
FIG. 2 depicts an actuator controller of a testing fixture for automated testing of PPG sensor devices using a rotational actuator in accordance with one or more embodiments of the present disclosure.

Referring now to FIG. 2, an actuator controller of a testing fixture for automated testing of PPG sensor devices using a rotational actuator is illustrated in accordance with one or more embodiments of the present disclosure.

In some embodiments, the actuator controller 116 may control the rotational actuator 120 based on a testing protocol 114 that represents a particular cardiac behavior represented by PPG sensor testing parameters. Accordingly, at block 201, the actuator controller 116 may receive the PPG sensor testing parameters representing the cardiac behavior via the testing protocol 114, as detailed above.

In some embodiments, at block 202, the actuator controller may generate actuation control parameters that define an actuation pattern. In some embodiments, the actuation pattern simulates the PPG sensor testing parameters representing the cardiac behavior.

In some embodiments, at block 203, the actuator controller 116 may generate rotational actuator control signal(s) based on the actuation control parameters as detailed above to control the rotational actuator according to the actuation pattern. The rotational actuator control signal(s) may include digital signals configured to cause the rotational actuator 120 to rotate to each position associated with the actuation pattern.

In some embodiments, the actuator controller 116 outputs the actuator control signals, via the DA converter 118, to the rotational actuator 120. As a result, the rotational actuator 120 is controlled to rotate the variable reflectivity disc 130 to present to the PPG sensor 140 a sequence of levels of reflectivity according to the actuation pattern to simulate the time-varying reflectivity of a subject's tissue when presenting the cardiac behavior.

Figure 3:
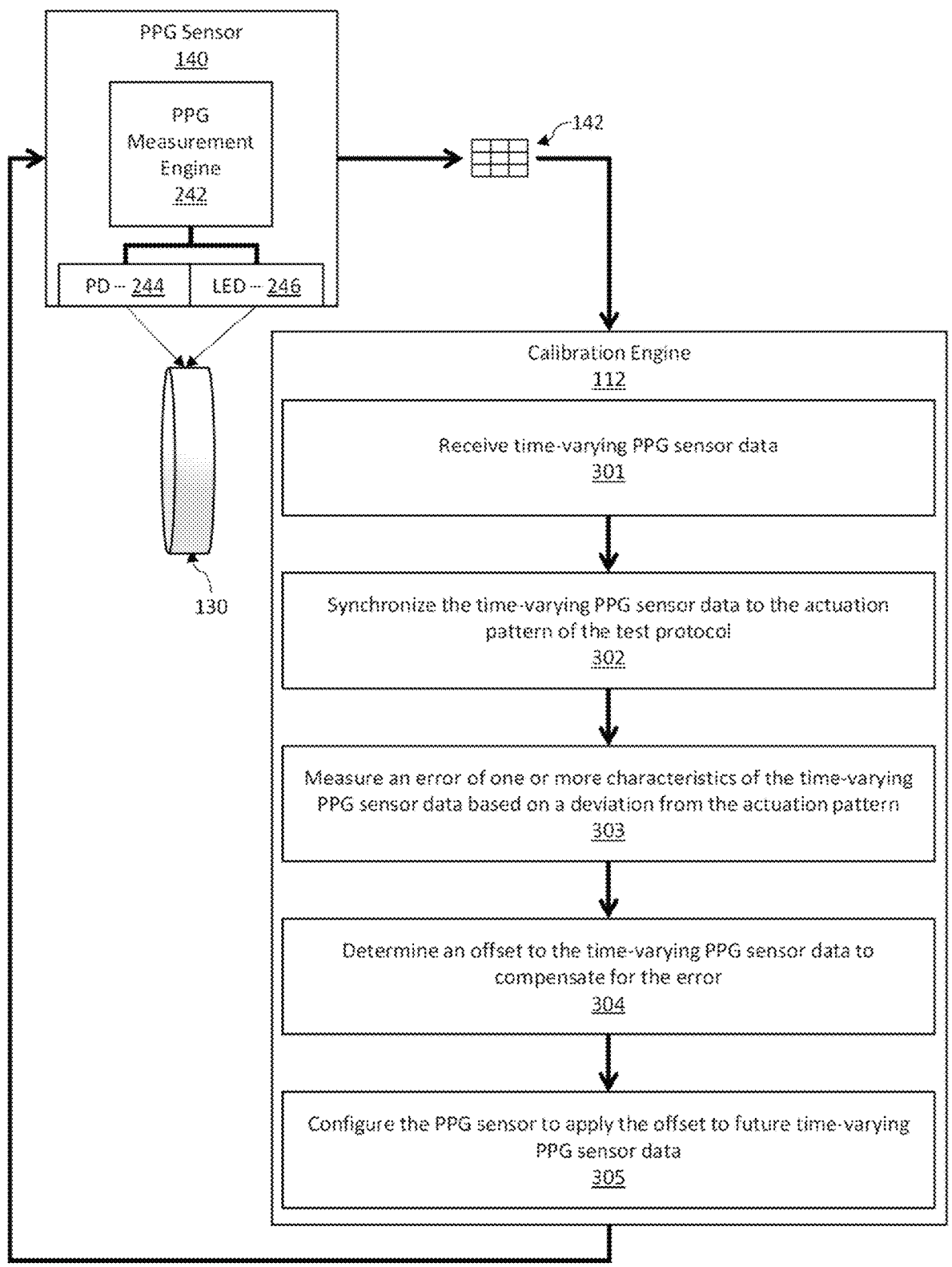
FIG. 3 depicts a calibration engine of a testing fixture for automated calibration of PPG sensor devices based on testing with a rotational actuator in accordance with one or more embodiments of the present disclosure.

Referring now to FIG. 3, a calibration engine of a testing fixture for automated calibration of PPG sensor devices based on testing with a rotational actuator is illustrated in accordance with one or more embodiments of the present disclosure.

In some embodiments, the PPG sensor 140 may include a PPG measurement engine 242 configured to measure light detected on a subject's tissue as a way to measure cardiac activity. To do so, the PPG sensor 140 may include a light emitting diode (LED) 246 and a photodetector (PD) 244. In some embodiments, the PPG sensor 140 may employ the LED 246 to inject light into the subject's tissue and the PD 244 to receive light that reflects and/or scatters and exits the tissue. A PPG signal include time-varying PPG sensor data 142 may include the amplitude of the reflected and/or scattered light that is modulated with volumetric change in blood volume in the tissue. In some embodiments, the LED 246 may be a green LED, red LED, or an infrared (IR) LED. When more than one light emitter is used, the plurality can include the same or different light emitters (with different emission wavelengths). For example, a combination of one or more green LEDs and IR LEDs may be used. In some variations, the light emitting diodes emit light with a peak spectral response between about 400 and 620 nm.

In some embodiments, at block 301, the calibration engine 112 may receive the time-varying PPG sensor data 142 of the PPG signal.

In some embodiments, at block 302, the calibration engine 112 may synchronize the time-varying PPG sensor data 142 to the actuation pattern of the test protocol 114. Thus, time in the time-varying PPG sensor data 142 may be aligned with time in the actuation pattern in order to directly compare the PPG measurements at each time point to the actuation control parameters of the actuation pattern at each time point.

In some embodiments, at block 303, the calibration engine 112 may measure an error in one or more characteristics of the time-varying PPG sensor data based on a deviation from the actuation pattern. The characteristic(s) may include, e.g., error in amplitude, error in duration, mismatch(es), among other sources of error or any combination thereof.

In some embodiments, at block 304, the calibration engine 112 may determine an offset to the time-varying PPG sensor data to compensate for the error.

In some embodiments, at block 305, the calibration engine 112 may configure the PPG sensor 140 to apply the offset to future time-varying PPG sensor data, thus compensating for the error in the time-varying PPG sensor data.

Figure 4:
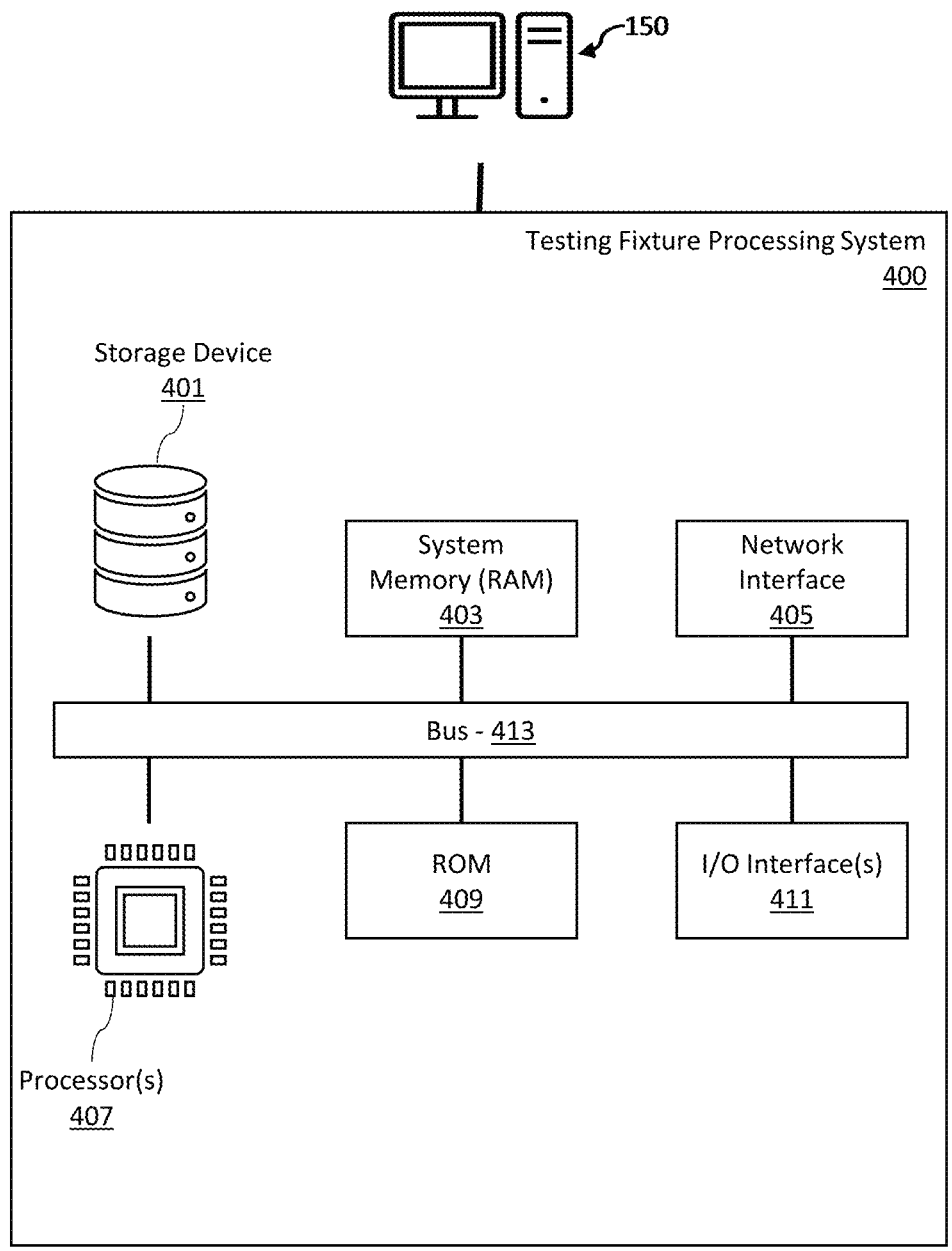
FIG. 4 depicts a processing system for a testing fixture for automated testing and calibration of PPG sensor devices in accordance with one or more embodiments of the present disclosure.

Referring now to FIG. 4, a processing system for a testing fixture for automated testing and calibration of PPG sensor devices is illustrated in accordance with one or more embodiments of the present disclosure.

The testing fixture processing system 400 may be a digital computer that, in terms of hardware architecture, generally includes a processor 409, input/output (I/O) interfaces 411, a network interface 405, a data store 401, and system memory (RAM) 403. It should be appreciated by those of ordinary skill in the art that FIG. 4 depicts the testing fixture processing system 400 in an oversimplified manner, and a practical embodiment may include additional components and suitably configured processing logic to support features described herein or known or conventional operating features that are not described in detail herein.

The components (409, 411, 405, 401, and 403) are communicatively coupled via a local interface 413. The local interface 413 may be, for example, but not limited to, one or more buses or other wired or wireless connections, as is known in the art. The local interface 413 may have additional elements, which are omitted for simplicity, such as controllers, buffers (caches), drivers, repeaters, and receivers, among many others, to enable communications. Further, the local interface 413 may include address, control, and/or data connections to enable appropriate communications among the aforementioned components.

The processor 409 is a hardware device for executing software instructions. The processor 409 may be any custom made or commercially available processor, a central processing unit (CPU), an auxiliary processor among several processors associated with the testing fixture processing system 400, a semiconductor-based microprocessor (in the form of a microchip or chip set), or generally any device for executing software instructions. When the testing fixture processing system 400 is in operation, the processor 409 is configured to execute software stored within the system memory (RAM) 403, to communicate data to and from the system memory (RAM) 403, and to generally control operations of the testing fixture processing system 400 pursuant to the software instructions. The I/O interfaces 411 may be used to receive user input from and/or for providing system output to one or more devices or components. User input may be provided via, for example, a keyboard, touchpad, and/or a mouse. System output may be provided via a display device and a printer (not shown). I/O interfaces 411 may include, for example, a serial port, a parallel port, a small computer system interface (SCSI), a serial ATA (SATA), a fiber channel, Infiniband, iSCSI, a PCI Express interface (PCI-x), an infrared (IR) interface, a radio frequency (RF) interface, and/or a universal serial bus (USB) interface.

The network interface 405 may be used to enable the testing fixture processing system 400 to communicate on a network, such as the cloud 12. The network interface 405 may include, for example, an Ethernet card or adapter (e.g., 10BaseT, Fast Ethernet, Gigabit Ethernet, 10 GbE) or a wireless local area network (WLAN) card or adapter (e.g., 802.11a/b/g/n/ac). The network interface 405 may include address, control, and/or data connections to enable appropriate communications on the network. A data store 401 may be used to store data. The data store 401 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 401 may incorporate electronic, magnetic, optical, and/or other types of storage media. In one example, the data store 401 may be located internal to the testing fixture processing system 400 such as, for example, an internal hard drive connected to the local interface 413 in the testing fixture processing system 400. Additionally, in another embodiment, the data store 401 may be located external to the testing fixture processing system 400 such as, for example, an external hard drive connected to the I/O interfaces 411 (e.g., SCSI or USB connection). In a further embodiment, the data store 401 may be connected to the testing fixture processing system 400 through a network, such as, for example, a network attached file server.

The system memory (RAM) 403 and/or the read only memory (ROM) 409 may include any of volatile memory elements (e.g., random access memory (RAM, such as DRAM, SRAM, SDRAM, etc.)), nonvolatile memory elements (e.g., ROM, hard drive, tape, CDROM, etc.), and combinations thereof. Moreover, the system memory (RAM) 403 may incorporate electronic, magnetic, optical, and/or other types of storage media. Note that the system memory (RAM) 403 may have a distributed architecture, where various components are situated remotely from one another but can be accessed by the processor 409. The software in system memory (RAM) 403 may include one or more software programs, each of which includes an ordered listing of executable instructions for implementing logical functions. The software in the system memory (RAM) 403 includes a suitable operating system (O/S) and one or more programs. The operating system controls the execution of other computer programs, such as the one or more programs, and provides scheduling, input-output control, file and data management, memory management, and communication control and related services. The one or more programs may be configured to implement the various processes, algorithms, methods, techniques, etc. described herein, such as related to the automated testing and/or calibration of the PPG sensor 140.

In some embodiments, the illustrative computer-based systems or platforms of the present disclosure may be configured to securely store and/or transmit data by utilizing one or more of encryption techniques (e.g., private/public key pair, Triple Data Encryption Standard (3DES), block cipher algorithms (e.g., IDEA, RC2, RC5, CAST and Skipjack), cryptographic hash algorithms (e.g., MD5, RIPEMD-160, RTR0, SHA-1, SHA-2, Tiger (TTH), WHIRLPOOL, RNGs).

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" can refer to a person who receives data provided by the data or service provider over the Internet in a browser session, or can refer to an automated software application which receives the data and stores or processes the data.

The aforementioned examples are, of course, illustrative and not restrictive.

While one or more embodiments of the present disclosure have been described, it is understood that these embodiments are illustrative only, and not restrictive, and that many modifications may become apparent to those of ordinary skill in the art, including that various embodiments of the inventive methodologies, the illustrative systems and platforms, and the illustrative devices described herein can be utilized in any combination with each other. Further still, the various steps may be carried out in any desired order (and any desired steps may be added and/or any desired steps may be eliminated).

What is claimed is:

1. A testing fixture comprising:
  a variable reflectivity disk positioned so as to have a patch of a surface of the variable reflectivity disk sensed by a photoplethysmogram (PPG) sensor;
    wherein the variable reflectivity disk comprises a plurality of portions of the surface;
    wherein each portion of the surface comprises a level of reflectivity;
  a rotational actuator configured to rotate the variable reflectivity disk such that the patch sensed by the PPG sensor shifts along the surface during rotation so as to move the plurality of portions of the surface with respect to the patch;
  an actuator controller configured to:
    receive a testing protocol comprising a plurality of PPG sensor testing parameters;
      wherein the plurality of PPG sensor testing parameters is representative of a cardiac behavior of a subject;
    generate an actuation pattern defined by the PPG sensor testing parameters;
      wherein the actuation pattern comprises a mapping of the PPG sensor testing parameters to a sequence of levels of reflectivity;
    generate an actuation control signal comprising a mapping of the sequence of levels of reflectivity to the plurality of positions on the surface of the variable reflectivity disk;
    control the rotational actuator according to the actuation pattern to rotate the variable reflectivity disk such that the patch sensed by the PPG sensor shifts through the plurality of portions on the surface to present the sequence of levels of reflectivity to the PPG sensor;
    receive a PPG signal comprising time-varying PPG sensor data representative of measurements of the plurality of portions on the surface;
    determine that the PPG sensor is defective based at least in part on an error of one or more characteristics of the time-varying PPG sensor data relative to the actuation pattern; and
    generate at least one alert to a user computing device to alert at least one user of that the PPG sensor is defective.

2. The testing fixture of claim 1, further comprising a calibration engine configured to:
  receive the PPG signal comprising time-varying PPG sensor data representative of measurements of the plurality of portions on the surface;
  determine an offset to the time-varying PPG sensor data based at least in part on the error of the one or more characteristics; and
  configure the PPG sensor to apply the offset to future time-varying PPG sensor data so as to compensate for the error.

3. The testing fixture of claim 1, wherein each portion of the surface comprises a gradient of levels of reflectivity.

4. The testing fixture of claim 1, wherein the plurality of portions is two portions, and the levels of reflectivity are two levels of reflectivity.

5. The testing fixture of claim 4, wherein the rotational actuator comprises a bidirectional rotational actuator; and
  wherein the actuation control signal is configured to cause the rotational actuator to rotate bidirectionally between the two portions so as to alternately present the two levels of reflectivity according to the actuation pattern.

6. The testing fixture of claim 1, wherein the actuation control signal comprises a digital signal having a predetermined bit depth.

7. The testing fixture of claim 6, further comprising a digital to analog converter configured to convert the actuation control signal to an analog signal to drive the rotational actuator according to the actuation pattern.

8. The testing fixture of claim 6, wherein the predetermined bit depth is associated with a number of levels of reflectivity of the actuation pattern.

9. A testing fixture comprising:
  receiving, by at least one processor, a testing protocol comprising a plurality of PPG sensor testing parameters for testing a photoplethysmogram (PPG) sensor with a variable reflectivity disk;
    wherein the variable reflectivity disk positioned so as to have a patch of a surface of the variable reflectivity disk sensed by PPG sensor;
    wherein the variable reflectivity disk comprises a plurality of portions of the surface;
    wherein each portion of the surface comprises a level of reflectivity;

wherein a rotational actuator is configured to rotate the variable reflectivity disk such that the patch sensed by the PPG sensor shifts along the surface during rotation so as to move the plurality of portions of the surface with respect to the patch;

wherein the plurality of PPG sensor testing parameters is representative of a cardiac behavior of a subject;

generating, by the at least one processor, an actuation pattern defined by the PPG sensor testing parameters;

wherein the actuation pattern comprises a mapping of the PPG sensor testing parameters to a sequence of levels of reflectivity;

generating, by the at least one processor, an actuation control signal comprising a mapping of the sequence of levels of reflectivity to the plurality of positions on the surface of the variable reflectivity disk;

controlling, by the at least one processor, the rotational actuator according to the actuation pattern to rotate the variable reflectivity disk such that the patch sensed by the PPG sensor shifts through the plurality of portions on the surface to present the sequence of levels of reflectivity to the PPG sensor;

receiving, by the at least one processor, a PPG signal comprising time-varying PPG sensor data representative of measurements of the plurality of portions on the surface;

determining, by the at least one processor, that the PPG sensor is defective based at least in part on an error of one or more characteristics of the time-varying PPG sensor data relative to the actuation pattern; and generating, by the at least one processor, at least one alert to a user computing device to alert at least one user of that the PPG sensor is defective.

10. The testing fixture of claim 9, further comprising:

receiving, by the at least one processor, the PPG signal comprising time-varying PPG sensor data representative of measurements of the plurality of portions on the surface;

determining, by the at least one processor, an offset to the time-varying PPG sensor data based at least in part on the error of the one or more characteristics; and configuring, by the at least one processor, the PPG sensor to apply the offset to future time-varying PPG sensor data so as to compensate for the error.

11. The testing fixture of claim 9, wherein each portion of the surface comprises a gradient of levels of reflectivity.

12. The testing fixture of claim 9, wherein the plurality of portions is two portions, and the levels of reflectivity are two levels of reflectivity.

13. The testing fixture of claim 12, wherein the rotational actuator comprises a bidirectional rotational actuator; and wherein the actuation control signal is configured to cause the rotational actuator to rotate bidirectionally between the two portions so as to alternately present the two levels of reflectivity according to the actuation pattern.

14. The testing fixture of claim 9, wherein the actuation control signal comprises a digital signal having a predetermined bit depth.

15. The testing fixture of claim 14, further comprising converting, by the at least one processor, the actuation control signal to an analog signal to drive the rotational actuator according to the actuation pattern.

16. The testing fixture of claim 14, wherein the predetermined bit depth is associated with a number of levels of reflectivity of the actuation pattern.

17. A testing fixture comprising:

a variable reflectivity disk positioned so as to have a patch of a surface of the variable reflectivity disk sensed by a photoplethysmogram (PPG) sensor;

wherein the variable reflectivity disk comprises a plurality of portions of the surface;

wherein each portion of the surface comprises a level of reflectivity;

a rotational actuator configured to rotate the variable reflectivity disk such that the patch sensed by the PPG sensor shifts along the surface during rotation so as to move the plurality of portions of the surface with respect to the patch;

an actuator controller configured to:

receive a testing protocol comprising a plurality of PPG sensor testing parameters;

wherein the plurality of PPG sensor testing parameters is representative of a cardiac behavior of a subject;

generate an actuation pattern defined by the PPG sensor testing parameters;

wherein the actuation pattern comprises a mapping of the PPG sensor testing parameters to a sequence of levels of reflectivity;

generate an actuation control signal comprising a mapping of the sequence of levels of reflectivity to the plurality of positions on the surface of the variable reflectivity disk; and control the rotational actuator according to the actuation pattern to rotate the variable reflectivity disk such that the patch sensed by the PPG sensor shifts through the plurality of portions on the surface to present the sequence of levels of reflectivity to the PPG sensor.

18. The testing fixture of claim 17, wherein each portion of the surface comprises a gradient of levels of reflectivity.

19. The testing fixture of claim 17, wherein the plurality of portions is two portions, and the levels of reflectivity are two levels of reflectivity.

20. The testing fixture of claim 19, wherein the rotational actuator comprises a bidirectional rotational actuator; and wherein the actuation control signal is configured to cause the rotational actuator to rotate bidirectionally between the two portions so as to alternately present the two levels of reflectivity according to the actuation pattern.

* * * * *